United States Patent
Kusunoki et al.

(10) Patent No.: US 10,604,654 B2
(45) Date of Patent: Mar. 31, 2020

(54) CURABLE RESIN COMPOSITION

(71) Applicant: Shin-Etsu Chemical Co., Ltd., Tokyo (JP)

(72) Inventors: Takayuki Kusunoki, Annaka (JP); Yuusuke Takamizawa, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 68 days.

(21) Appl. No.: 15/951,577

(22) Filed: Apr. 12, 2018

(65) Prior Publication Data

US 2018/0298150 A1 Oct. 18, 2018

(30) Foreign Application Priority Data

Apr. 13, 2017 (JP) ................. 2017-079831

(51) Int. Cl.
| | | |
|---|---|---|
| C08L 83/14 | (2006.01) | |
| H01L 33/56 | (2010.01) | |
| C08G 77/52 | (2006.01) | |
| C08K 5/54 | (2006.01) | |
| H01L 23/29 | (2006.01) | |
| H01L 33/50 | (2010.01) | |
| C08G 77/00 | (2006.01) | |
| C08G 77/60 | (2006.01) | |
| C07F 7/08 | (2006.01) | |

(52) U.S. Cl.
CPC .............. *C08L 83/14* (2013.01); *C08G 77/52* (2013.01); *C08K 5/5403* (2013.01); *H01L 23/296* (2013.01); *H01L 33/56* (2013.01); *C07F 7/0805* (2013.01); *C08G 77/60* (2013.01); *C08G 77/80* (2013.01); *H01L 33/507* (2013.01)

(58) Field of Classification Search
CPC combination set(s) only.
See application file for complete search history.

(56) References Cited

U.S. PATENT DOCUMENTS

| | | | |
|---|---|---|---|
| 6,368,535 B1 | 4/2002 | Katsoulis et al. | |
| 6,596,821 B1 * | 7/2003 | Katsoulis ............... | C08G 77/04 525/474 |

| | | | |
|---|---|---|---|
| 2005/0080154 A1 | 4/2005 | Tabei | |
| 2008/0070333 A1 | 3/2008 | Morita et al. | |
| 2009/0236759 A1 | 9/2009 | Kashiwagi | |

FOREIGN PATENT DOCUMENTS

| | | | |
|---|---|---|---|
| JP | 10-152615 A | * | 6/1998 |
| JP | 2001-064393 A | | 3/2001 |
| JP | 2005-133073 A | | 5/2005 |
| JP | 2006-093354 A | | 4/2006 |
| JP | 5136963 B2 | | 2/2013 |
| KR | 2015107978 A | * | 9/2015 |

OTHER PUBLICATIONS

Machine translation of KR 2015107978 (no date).*
Machine translation of JP 10-152615 (no date).*

* cited by examiner

*Primary Examiner* — Marc S Zimmer
(74) *Attorney, Agent, or Firm* — Birch, Stewart, Kolasch & Birch, LLP

(57) ABSTRACT

One of the purposes of the present invention is to provide a curable resin composition which has good curability and provides a cured product having a sufficient hardness, in particular an addition-curable organic silicon resin composition. The present invention provides a curable resin composition comprising the following components (A) to (C): (A) an organic-silicon compound having at least two alkenyl groups in a molecule, (B) an organic silicon compound which is represented by the formula (I) and has at least three hydrosilyl groups each bonded to the carbon atom of the benzene ring in an amount such that a ratio of the number of the hydrosilyl group in component (B) to the number of the alkenyl group in component (A) is 0.4 to 4,

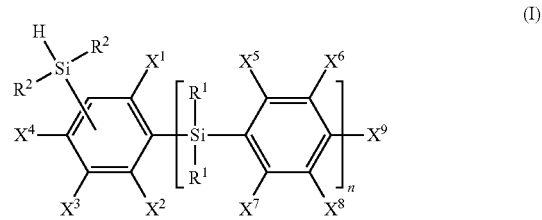

(I)

and (C) a hydrosilylation catalyst in a catalytic amount.

9 Claims, No Drawings

CURABLE RESIN COMPOSITION

CROSS REFERENCE

This application claims the benefits of Japanese Patent Application No. 2017-079831 filed on Apr. 13, 2017, the contents of which are hereby incorporated by reference.

FIELD OF THE INVENTION

The present invention relates to a curable resin composition and a semiconductor device provided with a cured product of the composition. Specifically, the present invention relates to an addition-curable organic silicon resin composition comprising an organic silicon compound having a silphenylene skeleton and at least three hydrosilyl groups in a molecule.

The addition-curable organic silicon resin composition has quick curability and provides a cured product having an excellent heat resistance and light resistance and, therefore, has been used as a material for encapsulating semiconductor elements such as LEDs. For instance, Japanese Patent No. 5136963, Patent literature 1, describes an addition-curable silicone resin composition which provides high adhesion to an LED package made of a thermoplastic resin such as PPA. Japanese Patent Application Laid-Open No. 2006-93354, Patent literature 2, describes a method for encapsulating an optical semiconductor element by compression molding of an addition-curable silicone resin composition.

As described above, addition curable organic silicon resin compositions are generally used as encapsulating materials for a semiconductor, but the properties are not satisfactory. In particular, in the field of encapsulating materials for a semiconductor, a stress is applied to the encapsulating resin due to external environment or a temperature rise during energization. Therefore, a material having an excellent crack resistance is required. However, crack resistance of the silicone resin is insufficient and there is a problem that cracks occur easily in a resin. In order to solve this problem, a soft silicone resin in the form of a gel or a rubber is used. However, the gel or rubber silicone resin is not suitable in the case of encapsulating a semiconductor by compression molding or transfer molding, because tackiness of the gel or rubber silicone resin is noticeable and, thereby, sticking to a mold occurs. Therefore, a silicone resin is required, which can withstand stresses while maintaining its hardness enough to remove a mold from the resin.

Japanese Patent Application Laid-Open Nos. 2001-64393 and 2005-133073, herein referred to as Patent literatures 3 and 4, describe that a silphenylene skeleton is incorporated in the resin in order to provide toughness to a cured product while maintaining its hardness. In these methods, the movement of the polymer chain is restricted by the introduced silphenylene skeleton, whereby the resin is made rigid and has high hardness.

PRIOR LITERATURES

Patent Literature 1: Japanese Patent No. 5136963
Patent Literature 2: Japanese Patent Application Laid-Open No. 2006-93354
Patent Literature 3: Japanese Patent Application Laid-Open No. 2001-64393
Patent Literature 4: Japanese Patent Application Laid-Open No. 2005-133073

SUMMARY OF THE INVENTION

The silphenylene has only two hydrosilyl groups bonded in the aforesaid patent literatures, when such is use as a molding material, the curing rate is too slow to attain sufficient hardness, so that the productivity is inferior. Further, silphenylene having only two hydrosilyl groups does not have a high boiling point enough to be used as such. Therefore, the silphenylene needs to be modified with a siloxane or an organic substance by a condensation reaction or a hydrosilylation reaction before used. The compound having the siloxane-modified silphenylene skeleton has softness and brittleness due to the introduced siloxane. The compound having the organic-modified silphenylene skeleton has poor heat resistance and light resistance. Therefore, these compounds are not suitable for an encapsulating material.

One of the purposes of the present invention is to provide a curable resin composition which has good curability and provides a cured product having a sufficient hardness. Specifically, the purpose of the present invention is to provide an addition-curable organic silicon resin composition.

The present inventors have made research and found that a curable resin composition comprising an organic silicon compound having three or more hydrosilyl groups and an organic silicon compound having two or more alkenyl groups attains the aforesaid purposes.

Thus, the present invention provides a curable resin composition comprising the following components (A) to (C):

(A) an organic silicon compound having at least two alkenyl groups in a molecule, (B) an organic silicon compound represented by the following formula (I) and having at least three hydrosilyl groups each bonded to a carbon atom of the benzene ring in an amount such that a ratio of the number of the hydrosilyl groups in component (B) to the number of the alkenyl groups in component (A) is 0.4 to 4,

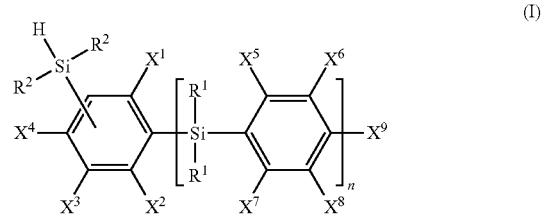

wherein n is 0 or 1, $X^1$ to $X^9$ are, independently of each other, a hydrogen atom, a monovalent hydrocarbon group having 1 to 6 carbon atoms or a group represented by the following formula (1') or (3'), $R^1$ is, independently of each other, a hydrogen atom, a monovalent hydrocarbon group having 1 to 12 carbon atoms or a group represented by the following formula (4'), and $R^2$ is, independently of each other, a hydrogen atom or a monovalent hydrocarbon group having 1 to 12 carbon atoms,

-continued

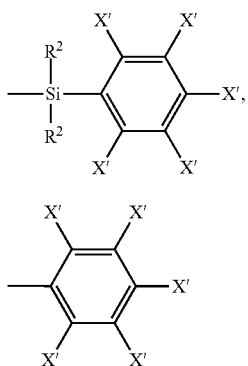

(3')

(4')

wherein R² is as defined above and X' is, independently of each other, a hydrogen atom, a monovalent hydrocarbon atom having 1 to 6 carbon atoms, or the group represented by the formula (1'), provided that at least two of the groups represented by $X^1$ to $X^9$ and X' are the group represented by the formula (1'), and (C) a hydrosilylation catalyst in a catalytic amount.

Effects of the Invention

The present curable resin composition comprising an organic silicon compound having three or more hydrosilyl groups reacts quickly to form cross-link and, therefore, has excellent curability, compared to an addition-curable organic silicon resin composition comprising an organic silicon compound having only two hydrosilyl groups. The cured product obtained from the present curable resin composition has a silphenylene skeleton and, thereby, has a better hardness, compared to a cured product obtained from an addition curable composition which does not have a silphenylene skeleton.

DETAILED DESCRIPTION OF THE INVENTION

The present invention will be described below in detail.

(A) Alkenyl Group-Containing Organic Silicon Compound

Component (A) is an organic silicon compound having at least two alkenyl groups in a molecule. The organic silicon compound may be any known alkenyl group-containing organopolysiloxane conventionally used in an addition reaction-curable siloxane resin composition. The organic silicon compound may or may not have a silphenylene skeleton. The organic silicon compound may be used singly or in combination of two or more of them.

The component (A) is preferably represented by the following formula (4):

$(R^4{}_3SiO_{1/2})_a(R^4{}_2SiO_{2/2})_b(R^4SiO_{3/2})_c(SiO_{4/2})_d(Y)_e(O_{1/2}R^3)_f$ (4), wherein $R^4$ is, independently of each other, a monovalent hydrocarbon group having 1 to 12 carbon atoms and optionally having an unsaturated bond, provided that at least two of $R^4$ are an alkenyl group, $R^3$ is a hydrogen atom or a monovalent hydrocarbon group having 1 to 6 carbon atoms, a is an integer of from 0 to 100, b is an integer of from 0 to 1,000, c is an integer of from 0 to 500, d is an integer of from 0 to 500, e is an integer of from 0 to 500, f is an integer of from 0 to 50, a total of a, b, c, d and e is 2 to 1,000, and Y is a silphenylene unit having a valance of 1 to 26 and is represented by the following formula (II),

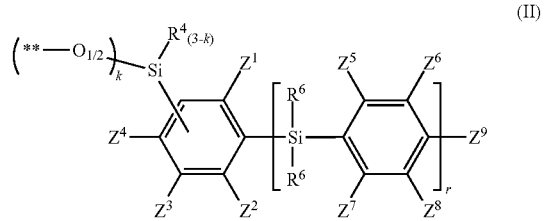

(II)

wherein r is 0 or 1, k is an integer of from 1 to 3, preferably 1, a bonding marked with ** in the formula (II) bonds to a silicon atom of another siloxane in the formula (4), $R^4$ is as defined above, $Z^1$ to $Z^9$ are, independently of each other, a hydrogen atom, a monovalent hydrocarbon group having 1 to 6 carbon atoms, a divalent, trivalent or tetravalent, preferably divalent, group represented by the following formula (5'), a monovalent group represented by the following formula (5''), or a group having a valance of 1 to 16, preferably 1 to 3 and represented by the following formula (7'), $R^6$ is, independently of each other, selected from the groups defined for $R^4$ or a group which has a valance of 1 to 16, preferably 1 to 3, and is represented by the following formula (6'),

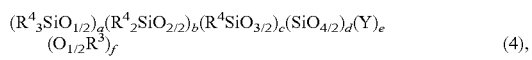

(5')

(5'')

wherein a bonding marked with * in the formulas (5') and (5'') bond to a carbon atom of the benzene ring, a bonding marked with ** in the formula (5') bonds to a silicon atom of another siloxane in the formula (4), k is an integer of from 1 to 3, k' is an integer of from 1 to 3, $R^4$ is as defined above, and $R^5$ is a monovalent hydrocarbon group having 1 to 6 carbon atoms, (7')

(6')

wherein Z' is, independently of each other, a hydrogen atom, a monovalent hydrocarbon group having 1 to 6 carbon atoms or a group represented by the formula (5') or (5"), $R^4$ is as defined above, a bonding marked with * in the formula (7') bonds to a carbon atom of the benzene ring and a bonding marked with *** in the formula (6') bonds to a silicon atom of another siloxane in the formula (4).

In the aforesaid formulas (6') and (7'), Z' is preferably a hydrogen atom, or a monovalent hydrocarbon group having 1 to 6 carbon atoms. When the formulas (6') or (7') have a group represented by the aforesaid formula (5'), one or two of Z' are preferably the divalent group represented by the formula (5').

$R^4$ is, independently of each other, a monovalent hydrocarbon group having 1 to 12 carbon atoms which may have an unsaturated bond, such as, for instance, a monovalent aliphatic saturated hydrocarbon group having 1 to 12 carbon atoms such as alkyl groups such as a methyl group, an ethyl group, a propyl group, a butyl group, a hexyl group; cycloalkyl groups such as a cyclohexyl group, a monovalent aromatic hydrocarbon group having 6 to 12 carbon atoms such as aryl groups such as a phenyl group, a tolyl group, a xylyl group and a naphthyl group and aralkyl groups such as a benzyl group, a phenylethyl group and a phenylpropyl group, and alkenyl groups such as a vinyl group, an allyl group and a propenyl group. At least two of $R^4$ are an alkenyl group. The alkenyl group is preferably a vinyl group. $R^4$ which is not an alkenyl group is preferably a methyl group or a phenyl group. $R^3$ is a hydrogen atom or a monovalent hydrocarbon group having 1 to 6 carbon atoms, such as, for instance, a monovalent aliphatic saturated hydrocarbon group such as alkyl groups such as a methyl group, an ethyl group, a propyl group, a butyl group and a hexyl group and cycloalkyl groups such as a cyclohexyl group, and a phenyl group. Among these, a hydrogen atom, a methyl group and an ethyl group are preferable.

Component (A) preferably has 0.005 to 0.5 mol, particularly 0.01 to 0.2 mol, of the alkenyl group, in 100 g of component (A). The alkenyl group may be present on $R^4_3SiO_{1/2}$ unit, $R^4_2SiO_{2/2}$ unit, and/or $R^4SiO_{3/2}$ unit, preferably on $R^4_3SiO_{1/2}$ unit.

a is an integer of from 0 to 100, preferably 0 to 75, further preferably 0 to 50. b is an integer of from 0 to 1,000, preferably 0 to 800, more preferably 0 to 500, further preferably 0 to 250. c is an integer of from 0 to 500, preferably 0 to 250, more preferably 0 to 125. d is an integer of from 0 to 500, preferably 0 to 250, more preferably 0 to 125. e is an integer of from 0 to 500, preferably 0 to 250, more preferably 0 to 125. f is an integer of from 0 to 50, preferably 0 to 40, more preferably 0 to 30. A total of a, b, c, d and e is 2 to 1,000, preferably 5 to 750, further preferably 10 to 500. k is an integer of from 1 to 3, preferably 1.

Component (A) preferably comprises at least one branched organopolysiloxane. In the branched organopolysiloxane, a total of c and d in the foresaid formula is preferably in the range of 5 to 750, further preferably 10 to 500. Further, preferred is a combination of the branched organopolysiloxane and the linear organopolysiloxane. A mass ratio of the branched organopolysiloxane to the linear organopolysiloxane is preferably 100:5 to 100:100, more preferably 100:10 to 100:50.

The organic silicon compound may be one produced by a known method or a commercially available product.

Y is a silphenylene unit having a valance of 1 to 26, preferably 1 to 12, and represented by the following formula (II). The group represented by the formula (II) is preferably such represented by the following formula (5), (6) or (7).

[Group Represented by the Following Formula (5)]

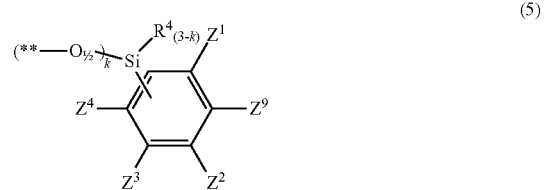

wherein $Z^1$ to $Z^4$ and $Z^9$ are, independently of each other, a hydrogen atom, a monovalent hydrocarbon group having 1 to 6 carbon atoms, a divalent, trivalent or tetravalent, preferably divalent, group, represented by the formula (5'), a monovalent group represented by the formula (5"), $R^4$, k and k' are as defined above. k is preferably 1. At least one of $Z^1$ to $Z^4$ and $Z^9$ is preferably the group represented by the formula (5') or (5"). In particular, at least two of $Z^1$ to $Z^4$ and $Z^9$ are the divalent group represented by the aforesaid formula (5').

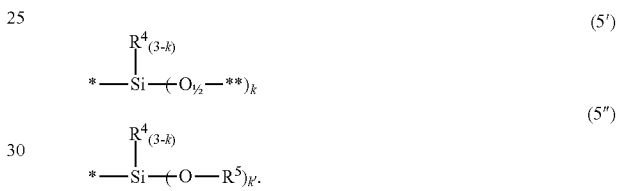

Examples of the group represented by the formula (5) include the group represented by the following formula.

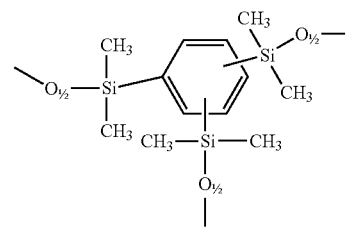

[Group Represented by the Following Formula (6)]

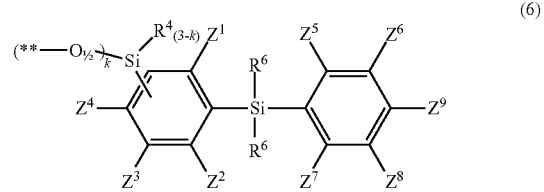

wherein $R^6$ is, independently of each other, selected from the groups defined for $R^4$ or a group having a valance of 1 to 16, preferably 1 to 3, which is represented by the following formula (6'). $R^4$ and k are as defined above. k is preferably 1. $Z^1$ to $Z^9$ and Z' are, independently of each other, a hydrogen atom, a monovalent hydrocarbon group having 1 to 6 carbon atoms, a divalent, trivalent or tetravalent, preferably divalent, group represented by the formula (5'), or a monovalent group represented by the formula (5"). At least one of $Z^1$ to $Z^9$ are preferably a divalent group represented by the formula (5'). The rest of $Z^1$ to $Z^9$ is preferably, independently of each other, a hydrogen atom or a monovalent hydrocarbon group having 1 to 6 carbon atoms, further preferably a hydrogen atom. $R^6$ is preferably, a methyl group or a group represented by the formula (6'). In the formula (6'), Z' is as defined above, preferably a hydrogen atom.

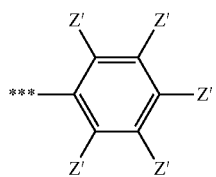
(6')

Examples of the group represented by the formula (6) include the group represented by the following formula.

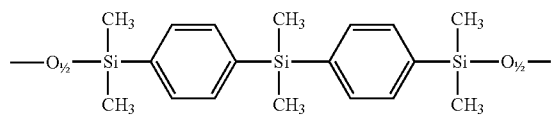

[Group Represented by the Following Formula (7)]

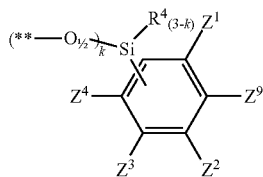
(7)

wherein $Z^1$ to $Z^4$ and $Z^9$ are, independently of each other, a hydrogen atom, a monovalent hydrocarbon group having 1 to 6 carbon atoms, or a group represented by the following formula (7'), Z' is, independently of each other, a hydrogen atom, a monovalent hydrocarbon group having 1 to 6 carbon atoms, a group represented by the formula (5'), or a group represented by the formula (5"), provided that at least two of Z to $Z^4$ and $Z^9$ are the group represented by the following formula (7'). $R^4$ and k are as defined above. k is preferably 1. At least one of $Z^1$ to $Z^9$ and Z' is preferably the divalent group represented by the aforesaid formula (5').

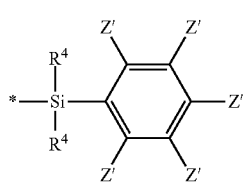
(7')

Examples of the group represented by the formula (7) include the group represented by the following formula.

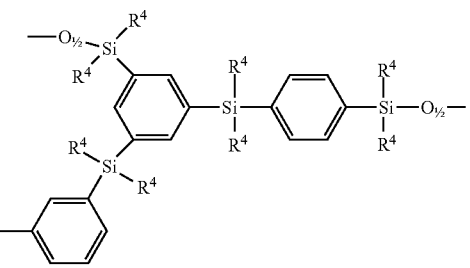

Examples of the monovalent hydrocarbon group having 1 to 6 carbon atoms in the formulas (5) to (7) include a monovalent aliphatic saturated hydrocarbon group such as an alkyl group such as a methyl group, an ethyl group, a propyl group, a butyl group, and a hexyl group and a cycloalkyl group such as a cyclohexyl group, and a phenyl group. Among these, a methyl group and an ethyl group are preferable.

[(B) Organic Silicon Compound Having at Least Three Hydrosilyl Groups]

Component (B) is the organic silicon compound which has at least three hydrosilyl groups each bonded to a carbon atom of the benzene ring and represented by the following formula (I).

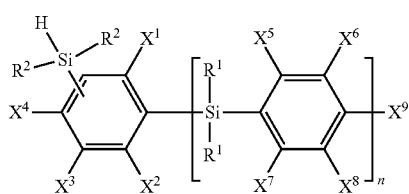
(I)

wherein n is 0 or 1, $X^1$ to $X^9$ are, independently of each other, a hydrogen atom, a monovalent hydrocarbon group having 1 to 6 carbon atoms or a group represented by the following formula (1') or (3'), $R^1$ is, independently of each other, a hydrogen atom, a monovalent hydrocarbon group having 1 to 12 carbon atoms or a group represented by the following formula (4'), and $R^2$ is, independently of each other, a hydrogen atom or a monovalent hydrocarbon group having 1 to 12 carbon atoms,

(1')

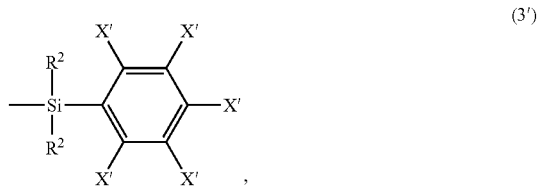
(3')

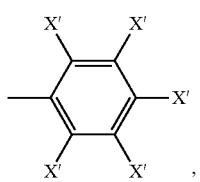

wherein $R^2$ is as defined above and X' is, independently of each other, a hydrogen atom, a monovalent hydrocarbon atom having 1 to 6 carbon atoms, or the group represented by the formula (1'), provided that at least two of the groups represented by $X^1$ to $X^9$ and X' are the group represented by the formula (1').

The monovalent hydrocarbon group having 1 to 12 carbon atoms is preferably a hydrocarbon group which does not have an aliphatic unsaturated bond, such as alkyl groups such as a methyl group, an ethyl group, a propyl group, a butyl group, a pentyl group, a hexyl group and an octyl group; cycloalkyl groups such as a cyclohexyl group; aryl groups such as a phenyl group, a tolyl group, a xylyl group and a naphthyl group; aralkyl groups such as a benzyl group, a phenylethyl group and a phenylpropyl group. $R^2$ is preferably a methyl group.

Examples of a monovalent hydrocarbon group having 1 to 6 carbon atoms in the groups $X^1$ to $X^9$ and X' include alkyl groups such as a methyl group, an ethyl group, a propyl group, a butyl group, and a hexyl group, cycloalkyl groups such as a cyclohexyl group, and a phenyl group. $X^1$ to $X^9$ and X' are preferably a hydrogen atom or a group represented by the aforesaid formula (1').

Preferred are compounds represented by the following formula (1), (2) or (3).

[Compound Represented by the Following Formula (1)]

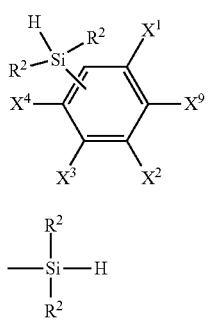

wherein $R^2$ is as defined above, $X^1$ to $X^4$ and $X^9$ are, independently of each other, a hydrogen atom, a monovalent hydrocarbon group having 1 to 6 carbon atoms or a group represented by the formula (1'), and at least two of $X^1$ to $X^4$ and $X^9$ are the group represented by the formula (1'). $X^1$ to $X^4$ and $X^9$ are preferably a hydrogen atom or the group represented by the aforesaid formula (1'). The all of the $X^1$ to $X^4$ and $X^9$ may be the group represented by the formula (1').

Examples of the compound represented by the formula (1) include organic silicon compounds represented by the following formulas.

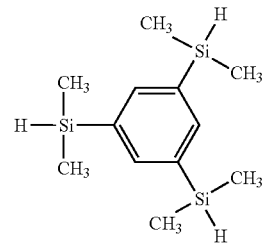

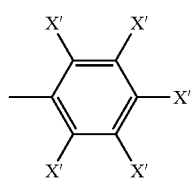

[Compound Represented by the Following Formula (2)]

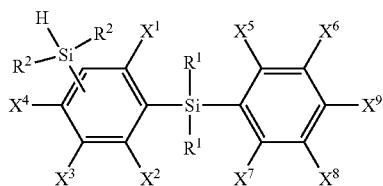

wherein $R^1$ is, independently of each other, a hydrogen atom, a monovalent hydrocarbon group having 1 to 12 carbon atoms or the group represented by the formula (4'), $R^2$ is as defined above, $X^1$ to $X^9$ and X' are, independently of each other, a hydrogen atom, a monovalent hydrocarbon group having 1 to 6 carbon atoms or a group represented by the formula (1'), and at least two of $X^1$ to $X^9$ and X' are the group represented by the formula (1'). Preferred are a compound wherein at least one of $R^1$ is a group represented by the formula (4') and the other $R^1$ is a hydrogen atom or a monovalent hydrocarbon group having 1 to 12 carbon atoms, a compound wherein both of $R^1$ are the groups represented by the formula (4'), and a compound wherein both of $R^1$ is a monovalent hydrocarbon group having 1 to 12 carbon atoms. Further, $X^1$ to $X^9$ and X' are preferably a hydrogen atom or the group represented by the formula (1'). All of the $X^1$ to $X^9$ and X' may be the group represented by the formula (1').

Examples of the compound represented by the formula (2) include organic silicon compounds represented by the following formulas.

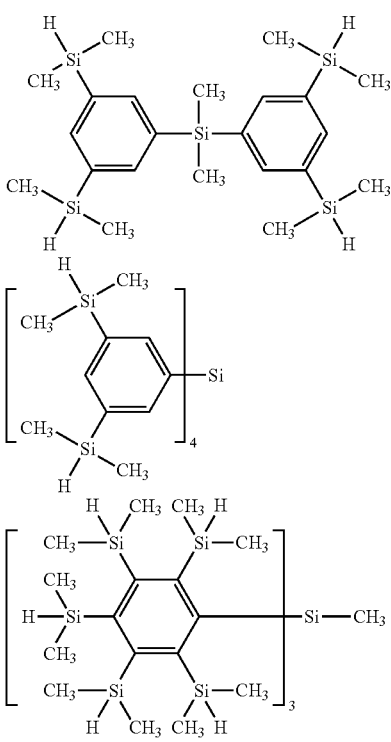

[Compound Represented by the Following Formula (3)]

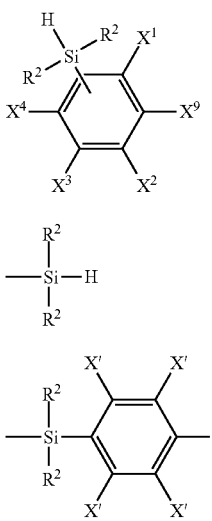

wherein $R^2$ is as defined above, $X^1$ to $X^4$ and $X^9$ are, independently of each other, a hydrogen atom, a monovalent hydrocarbon group having 1 to 6 carbon atoms or a group represented by the formula (1') or (3'), and X' is, independently of each other, a hydrogen atom, a monovalent hydrocarbon group having 1 to 6 carbon atoms or a group represented by the formula (1'), provided that at least two of $X^1$ to $X^4$ and $X^9$ are the group represented by the formula (3'). Preferably, the residues, $X^1$ to $X^4$ and $X^9$ and X', are a hydrogen atom or the group represented by the formula (1'), and at least two of $X^1$ to $X^4$ and $X^9$ are the group represented by the formula (1').

An Example of the compound represented by the formula (3) is organic silicon compounds represented by the following formula.

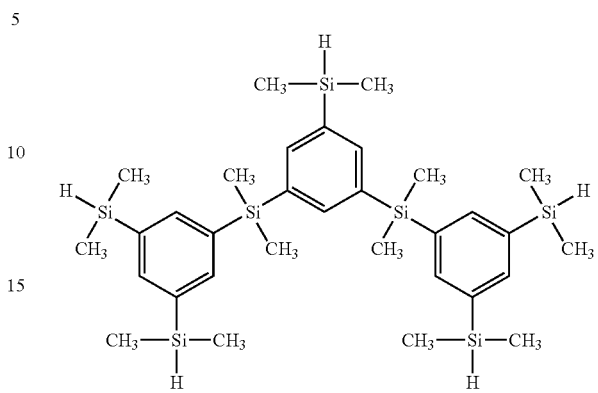

The present component (B) has at least three hydrogen atoms each bonded to a silicon atom, i.e., SiH groups. Preferably, component (B) has 0.15 to 3 mols, more preferably 0.3 to 1.5 mols, of SiH groups in 100 g of component (B).

An amount of component (B) is such that a ratio of the number of the hydrogen atoms each bonded to the silicon atom, i.e. hydrosilyl groups, in component (B) to the number of the alkenyl groups in component (A) is 0.4 to 4, preferably 0.6 to 2.5, further preferably 0.8 to 2.2. If the amount is less than the aforementioned lower limit, the amount of SiH group is insufficient so that curing does not proceed satisfactorily. If the amount exceeds the aforementioned upper limit, unreacted SiH groups cause a side reaction such as dehydrogenation, which is not preferred. When the composition comprises component (D) described below, the amount of component (B) may be such that a ratio of the total number of the hydrosilyl groups in components (B) and (D) to the number of the alkenyl groups in component (A) is in the aforesaid range.

Component (B) may be used singly or two or more in combination. Component (B) may be one produced by any known method or a commercially available product.

[(C) Hydrosilylation Catalyst]

Component (C) is a hydrosilylation catalyst which promotes the addition reaction of the alkenyl group of component (A) with the hydrosilyl group of component (B). Any known catalyst may be used and not particularly limited. Preferred is a catalyst selected from an element of the platinum group metals and a compound including an element of the platinum group metals. Examples of these catalysts include platinum catalysts such as platinum, including platinum black, platinum chloride, a chloroplatinic acid, a complex of platinum with an olefin such as a complex of platinum with a divinylsiloxane, and a complex of a platinum with a carbonyl; palladium catalysts; and rhodium catalysts. The catalyst may be used singly or in combination of them. Preferred are chloroplatinic acid and a complex of platinum with an olefin such as a complex of platinum with divinylsiloxane.

Component (C) may be used in a catalytic amount. The catalytic amount is such as to accelerate the hydrosilylation of components (A) and (B) and may properly be decided, depending on a desired curing rate. For instance, when a platinum group metal catalyst is used, the amount, reduced to a platinum group metal, is preferably 0.1 to 50 ppm, more preferably 1 to 10 ppm, relative to the total mass of the composition, in view of reactivity.

[(D) Organic Silicon Compound Having Two Hydrogen Atoms Each Bonded to a Silicon Atom]

The present curable resin composition may comprise an organic silicon compound having two hydrogen atoms each bonded to a silicon atom, together with component (B), in order to control the crosslink density. Component (D) may be one produced by any known method or a commercially available product. The hydrogen atoms each bonded to a silicon atom is preferably at the both terminals of a linear organic silicon compound such as one represented by the following formula (8) or (9).

wherein $R^4$ is a monovalent hydrocarbon group having 1 to 12 carbon atoms, W is a substituent represented by the following general formula (8'), g is an integer of from 0 to 50, h is an integer of from 0 to 50, and a total of g and h is 1 to 50.

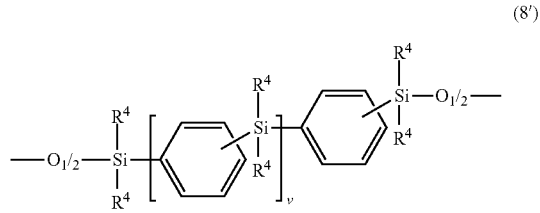

wherein $R^4$ is as defined above, v is an integer of from 0 to 3.

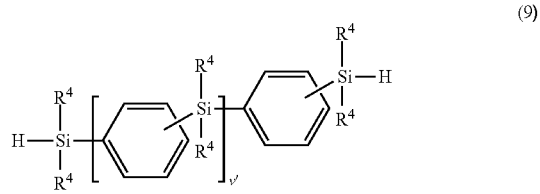

wherein $R^4$ is as defined above, v' is an integer of from 0 to 3.

In the formulas (8) and (9), $R^4$ is a monovalent hydrocarbon group having 1 to 12 carbon atoms, such as, for instance, a monovalent aliphatic saturated hydrocarbon group having 1 to 12 carbon atoms, such as alkyl groups such as a methyl group, an ethyl group, a propyl group, a butyl group and a hexyl group, and cycloalkyl groups such as a cyclohexyl group; and a monovalent aromatic hydrocarbon group having 6 to 12 carbon atoms such as aryl groups such as phenyl, tolyl, xylyl and naphthyl groups; aralkyl groups such as a benzyl group, a phenylethyl group and a phenylpropyl group. A methyl group and a phenyl group are preferable.

Component (D) has the hydrogen atoms each bonded to a silicon atom, i.e. SiH groups, at both terminals of the linear organosiloxane. Component (D) preferably has 0.005 to 0.5 mol, more preferably 0.01 to 0.2 mol, of SiH groups, in 100 g of component (D).

g is an integer of from 0 to 50, preferably 0 to 25, further preferably 0 to 10. h is an integer of from 0 to 50, preferably 0 to 10, more preferably 0 to 5. A total of g and h is 1 to 50, preferably 1 to 25, further preferably 1 to 10. v is an integer of from 0 to 3, preferably 0 or 1. v' is an integer of from 0 to 3, preferably 0 or 1.

The compounding ratio of components (B) to (D) may be in a range where the component (B) does not impair the effect of improving the curing rate. Preferably, a percentage of component (B) is 10 to 100%, more preferably 25 to 100%, further preferably 50 to 100%, relative to a total mass of components (B) and (D).

The present curable silicon resin composition may further comprise other additives such as a fluorescent material, an inorganic filler, an adhesion-imparting agent, and a curing inhibitor in addition to components (A) to (D), if needed. Each of component will be explained below in detail.

Fluorescent Material

The present fluorescent material is not particularly limited and any conventional fluorescent material may be used. For instance, preferred is such that absorbs light generated by a light-emitting semiconductor diode having a semiconductor element as a light emitting layer, in particular a nitride semiconductor element, and converts a wavelength of the absorbed light. The fluorescent material is preferably selected from, for instance, the group consisting of nitride fluorescent materials and oxynitride fluorescent materials which are activated mainly by lanthanide elements such as Eu and Ce; alkaline earth metal halogen apatite, alkaline earth metal borate halogen, alkaline earth metal aluminate, alkaline earth metal silicate, alkaline earth metal sulfide, alkaline earth metal thiogallate, alkaline earth metal silicon nitride and germinate fluorescent materials activated mainly by lanthanide elements such as Eu or by transition metal elements such as Mn; rare earth metal aluminate and rare earth metal silicate fluorescent materials which are activated mainly by lanthanide elements such as Ce; organic fluorescent materials and organic complex fluorescent materials which are activated mainly by lanthanide elements such as Eu; and Ca—Al—Si—O—N type oxynitride glass fluorescent materials.

Examples of the nitride fluorescent materials which are activated mainly by lanthanide elements such as Eu and Ce include $M_2Si_5N_8$:Eu, $MSi_7N_{10}$:Eu, $M_{1.8}Si_5O_{0.2}N_8$:Eu, and $M_{0.9}Si_7O_{0.1}N_{10}$:Eu, wherein M is at least one selected from the group consisting of Sr, Ca, Ba, Mg and Zn.

Examples of the oxynitride fluorescent materials which are activated mainly by lanthanide elements such as Eu and Ce include $MSi_2O_2N_2$:Eu, wherein M is at least one selected from the group consisting of Sr, Ca, Ba, Mg and Zn.

Examples of the alkaline earth metal halogen apatite fluorescent materials which are activated mainly by lanthanide elements such as Eu or transition metal elements such as Mn include $M_5(PO_4)_3X$:R', wherein M is at least one selected from the group consisting of Sr, Ca, Ba, Mg and Zn, X is at least one selected from the group consisting of F, Cl, Br and I, and R' is at least one of Eu and Mn.

Examples of the alkaline earth metal halogen borate fluorescent materials include $M_2B_5O_9X$:R', wherein M is at least one selected from the group consisting of Sr, Ca, Ba, Mg and Zn, X is at least one selected from the group consisting of F, Cl, Br and I, and R' is at least one of Eu and Mn.

Examples of the alkaline earth metal aluminate fluorescent materials include $SrAl_2O_4$:R', $Sr_4Al_{14}O_{25}$:R', $CaAl_2O_4$:R', $BaMg_2Al_{16}O_{27}$:R', $BaMg_2Al_{16}O_{12}$:R' and $BaMgAl_{10}O_{17}$:R', wherein R' is at least one of Eu and Mn.

Examples of the alkaline earth metal sulfide fluorescent materials include $La_2O_2S$:Eu, $Y_2O_2S$:Eu and $Gd_2O_2S$:Eu.

Examples of the rare earth metal aluminate fluorescent materials which are activated mainly by lanthanide elements such as Ce include YAG type fluorescent materials represented by compositional formulas: $Y_3Al_5O_{12}$:Ce, $(Y_{0.8}Gd_{0.2})_3Al_5O_{12}$:Ce, $Y_3(Al_{0.8}Ga_{0.2})_5O_{12}$:Ce, and $(Y,Gd)_3(Al,Ga)_5O_{12}$ and those compounds where a part or the whole of Y are replaced with Tb or Lu, such as $Tb_3Al_5O_{12}$:Ce and $Lu_3Al_5O_{12}$:Ce.

Examples of other fluorescent materials include ZnS:Eu, $Zn_2GeO_4$:Mn and $MGa_2S_4$:Eu, wherein M is at least one selected from the group consisting of Sr, Ca, Ba, Mg and Zn.

The aforementioned fluorescent materials may comprise at least one selected from the group consisting of Tb, Cu, Ag, Au, Cr, Nd, Dy, Co, Ni and Ti, in place of Eu or in addition to Eu, if needed.

The Ca—Al—Si—O—N type oxynitride glass fluorescent material comprises, as a matrix, oxynitride glass comprising 20 to 50 mole % of $CaCO_3$, calculated as CaO, 0 to 30 mole % of $Al_2O_3$, 25 to 60 mole % of $SiO$, 5 to 50 mole % of AlN and 0.1 to 20 mole % of rare earth metal oxides or transition metal oxides, wherein the total amount of the aforesaid components is 100 mole %. The fluorescent material with the oxynitride glass matrix preferably comprises nitrogen atoms in an amount of 15 mole % or less and preferably comprises, besides rare earth metal oxides ions, the other rare earth metal ions, as a co-activator, which work as a sensitizer in an amount of 0.1 to 10 mole %, calculated as rare earth metal oxides, in the fluorescent glass.

Other fluorescent materials which have a similar function and provide similar effects may be used.

The fluorescent material preferably has a mean diameter of 10 nm or more, more preferably 10 nm to 10 μm, further preferably 10 nm to 1 μm. The mean diameter is determined from a particle size distribution obtained in a laser diffraction method using a Cilas laser measurement instrument.

An amount of the fluorescent materials is preferably 0.1 to 2,000 parts by mass, more preferably 0.1 to 100 parts by mass, relative to 100 parts by mass of the components other than the fluorescent material, for instance, 100 parts by mass of components (A) to (C) and optionally component (D). When the present cured product is used as a wavelength conversion film comprising a fluorescent material, the amount of the fluorescent material is preferably 10 to 2,000 parts by mass.

Inorganic Filler

Examples of the inorganic filler include silica, fumed silica, fumed titanium dioxide, alumina, calcium carbonate, calcium silicate, titanium dioxide, iron (III) oxide and zinc oxide. The inorganic filler may be used singly or in combination of two or more of them.

An amount of the inorganic filler may be 20 parts by mass or less, preferably 0.1 to 10 parts by mass, relative to total 100 parts by mass of components (A) to (C) and optionally component (D), but not limited to these.

Adhesion-Imparting Agent

The present curable resin composition may comprise an adhesion-imparting agent in order to add adhesiveness to a cured product, if needed. Examples of the adhesion-imparting agent include organosiloxane oligomers having at least one selected from a hydrogen atom bonded to a silicon atom and an alkenyl group, and at least one selected from a hydroxysilyl group, an alkoxy group, an epoxy group or a nitrogen atom-containing substituent. The organosiloxane oligomer preferably has 4 to 50 silicon atoms, more preferably 4 to 20 silicon atoms. This organosiloxane oligomer is different from component (A) in that the former has a hydroxysilyl group, an alkoxy group, an epoxy group or a nitrogen atom-containing substituent.

The adhesion-imparting agent may be organooxysilyl-modified isocyanurate represented by the following general formula (10) or its hydrolysis and condensation product, i.e., organosiloxane-modified isocyanurate.

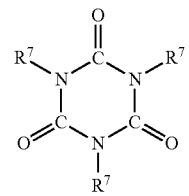

(10)

In formula (10), $R^7$ is, independently of each other, an organic group represented by the following formula (11) or a monovalent, unsaturated aliphatic hydrocarbon group which may comprise an oxygen atom, provided that at least one of $R^7$ is the group represented by the formula (11).

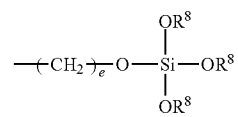

(11)

wherein $R^8$ is a hydrogen atom or a monovalent hydrocarbon group having 1 to 6 carbon atoms, such as a methyl or ethyl group, and e is an integer of from 1 to 6, preferably 1 to 4.

The monovalent, unsaturated aliphatic hydrocarbon group is preferably a linear or branched alkenyl group having 2 to 8 carbon atoms, further preferably 2 to 6 carbon atoms, such as a vinyl group, an allyl group, a 1-butenyl group, a 1-hexenyl group, a 2-methylpropenyl group and a (meth) acryl group.

An amount of the adhesion-imparting agent is preferably 10 parts by mass or less, more preferably 0.1 to 8 parts by mass, further preferably 0.2 to 5 parts by mass, relative to total 100 parts by mass of components (A) to (C) and optionally component (D). When the amount of the adhesion-imparting agent is within the aforesaid range, the effect of the present invention is not obstructed and the adhesive property is improved.

The amount of the adhesion-imparting agent is preferably such that a ratio of the total number of hydrosilyl groups in the composition to the total number of alkenyl groups in the composition is 0.4 to 4, more preferably 0.6 to 3, further preferably 0.8 to 2.

Curing Inhibitor

The present curable resin composition may further comprise a curing inhibitor in order to suppress the reactivity to improve storage stability. Examples of the curing inhibitor include triallylisocyanurate, alkyl maleates, acetylene alcohols, silane-modified or siloxane-modified product of these, hydroperoxides, tetramethylethylenediamine, benzotriazole and a mixture of them.

An amount of the curing inhibitor is preferably 0.001 to 1 part by mass, further preferably 0.005 to 0.5 part by mass, relative to the total 100 parts by mass of components (A) to (C) and optionally component (D).

Other Additives

The present curable resin composition may comprise other additives besides the aforesaid components. Examples of the other additives include anti-aging agents, radical polymerization inhibitors, flame retardants, surfactants, antiozonants, light stabilizers, thickeners, plasticizers, antioxidants, heat stabilizers, electrical conductivity-imparting agents, antistatic agents, radiation insulating agents, nucleating agents, phosphorus-type peroxide decomposers, lubricants, pigments, metal-inactivating agents, physical property-adjusting agents and organic solvents. These optional components may be used singly or in combination of two or more of them.

The simplest embodiment of the present curable resin composition consists of components (A), (B) and (C). In particular, it is preferred that the composition does not comprise any inorganic filler such as silica, in order to prepare a cured product having high transparency. The inorganic filler is as described above.

The present curable resin composition may be prepared in any known manners. For instance, the composition may be prepared by mixing component (A), component (B), component (C) and the other optional components in any manner. For instance, the aforesaid components are placed in a commercial stirrer, such as THINKY CONDITIONING MIXER, ex Thinky Corporation, and mixed homogeneously for about 1 to 5 minutes to prepare the present curable resin composition.

The present curable resin composition may be cured in any known manners. Curing conditions are not particularly limited. For instance, the composition may be cured at 60 to 180 degrees C. for 1 to 12 hours. In particular, the composition is cured stepwise. The stepwise curing preferably consists of the following two steps. The curable resin composition is first heated at 60 to 100 degrees C. for 0.5 to 2 hours to be defoamed sufficiently. Subsequently, the composition is heated at 120 to 180 degrees C. for 1 to 10 hours to cure. Through these steps, the composition is sufficiently cured, no bubble occur and the cured product is colorless and transparent, even when a cured product has a large thickness. In the present specification, "colorless and transparent" means that a light transmittance at 450 nm of a cured product having a thickness of 1 mm is 80% or more, preferably 85% or more, particularly preferably 90% or more.

The curable resin composition provides a cured product having a high optical transparency. Accordingly, the present silicone composition is useful as an encapsulating material for LED elements, in particular blue LED elements and violet LED elements. The encapsulation of LED elements with the present silicone composition may be carried out in any known manners. For instance, a dispense method and a compression molding method may be used.

On account of the properties such as excellent crack resistance, heat resistance, light resistance and transparency, the present curable resin composition and cured product are useful also as materials for displays, optical recording mediums, optical apparatus, optical components and optical fibers, and photo/electron functional organic materials and materials for integrated semiconductor circuit-related elements.

EXAMPLES

The present invention will be explained below in further detail with reference to a series of the Examples and the Comparative Examples, though the present invention is in no way limited by these Examples.

In the following descriptions, the weight average molecular weight (Mw) was determined by gel permeation chromatography, GPC, and reduced to polystyrene. Conditions in the GPC were as follows.
[GPC Conditions]
Developing Solvent: Tetrahydrofuran
Flow rate: 0.6 mL/min.
Columns: all provided by TOSOH Cop.
TSK Guardcolumn SuperH-L
TSKgel SuperH4000 (6.0 mmI.D.×15 cm×1)
TSKgel SuperH3000 (6.0 mmI.D.×15 cm×1)
TSKgel SuperH2000 (6.0 mmI.D.×15 cm×2)
Column Temperature: 40 degrees C.
Injection Volume: 20 micro liters of a 0.5% by mass solution in tetrahydrofuran.
Detector: Differential refractive index detector (RI)

An amount of a vinyl (Vi) group (mol/100 g) and an amount of an SiH group (mol/100 g) were calculated from an integrated area for hydrogen atoms in $^1$H-NMR spectra at 400 MHz with dimethylsulfoxide as an internal standard. The $^1$H-NMR spectra was obtained with ULTRASHIELD™ 400PLUS, ex BRUKER Corporation.

Components (A), (B) and (C) used in the following Examples and Comparative Examples are as follows.
(A-1) Phenyl silicone resin which is represented by the following formula, and has a Vi group content of 0.15 mol/100 g and a weight-average molecular weight of 1,563, ex Shin-Etsu Chemical Co., Ltd.:

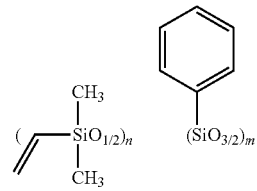

wherein a ratio of n to m is 0.22:0.78.
(A-2) Silphenylene skeleton-containing silicone resin which is represented by the following formula, and has a Vi group content of 0.19 mol/100 g and a weight-average molecular weight of 2,080, ex Shin-Etsu Chemical Co., Ltd.:

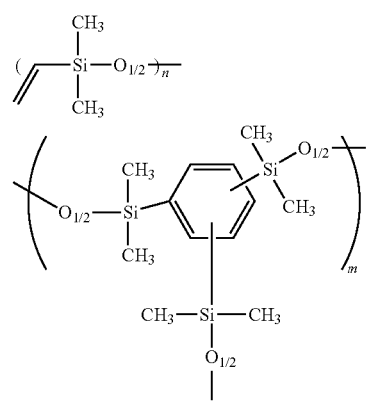

wherein a ratio of n to m is 0.4:0.6.
(A-3) Phenyl silicone oil having vinyl groups at both terminals, which is represented by the following formula, and has a Vi group content of 0.038 mol/100 g and a weight-average molecular weight of 5,729, ex Shin-Etsu Chemical Co., Ltd.:

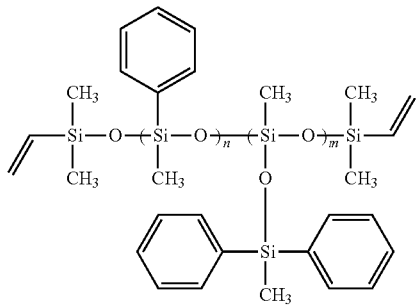

wherein a ratio of n to m is 0.03:0.97.

(A-4) Phenyl silicone oil having vinyl groups at both terminals, which is represented by the following formula, and has a Vi group content of 0.038 mol/100 g and a weight-average molecular weight of 5,562, ex Shin-Etsu Chemical Co., Ltd.:

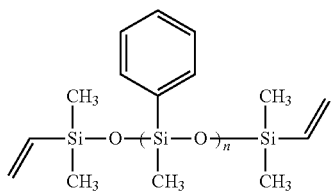

wherein n is 38 on average.

(A-5) Organic silicon compound having vinyl groups at both terminals, which is represented by the following formula, and has a Vi group content of 0.027 mol/100 g and a weight-average molecular weight of 7,433, ex Shin-Etsu Chemical Co., Ltd.:

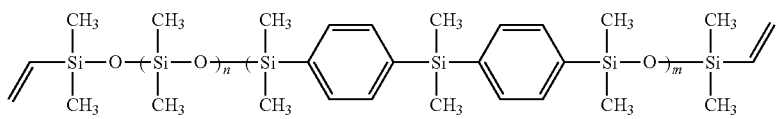

wherein a ratio of n to m is 0.67:0.33.

(B-1) Silphenylene skeleton-containing organic silicon compound which is represented by the following formula, and has a SiH group content of 1.2 mol/100 g and a weight-average molecular weight of 263, ex Shin-Etsu Chemical Co., Ltd.:

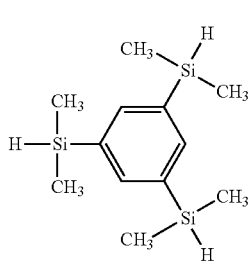

(B-2) Silphenylene skeleton-containing organic silicon compound which is represented by the following formula, and has a SiH group content of 0.90 mol/100 g and a weight-average molecular weight of 461, ex Shin-Etsu Chemical Co., Ltd.:

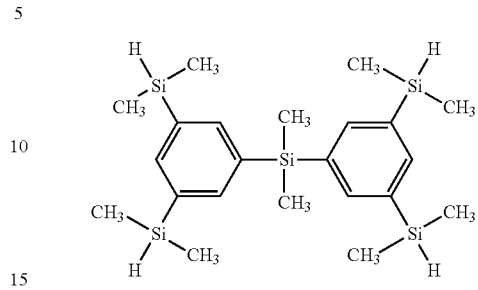

(B-3) Silphenylene skeleton-containing organic silicon compound which is represented by the following formula, and has a SiH group content of 0.78 mol/100 g and a weight-average molecular weight of 667, ex Shin-Etsu Chemical Co., Ltd.:

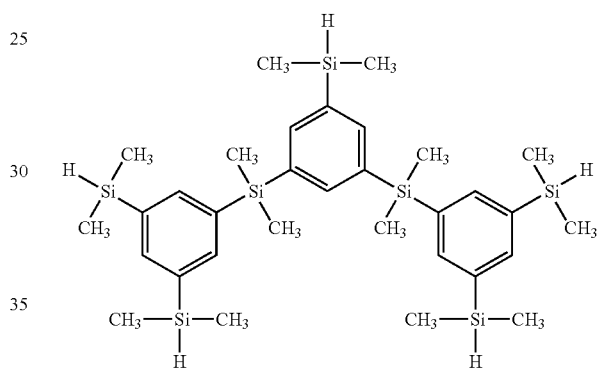

(B-4) Silphenylene skeleton-containing organic silicon compound which is represented by the following formula, and has a SiH group content of 1.0 mol/100 g and a weight-average molecular weight of 832, ex Shin-Etsu Chemical Co., Ltd.:

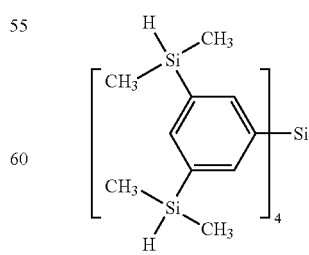

(B-5) Silphenylene skeleton-containing organic silicon compound which is represented by the following formula, has a SiH group content of 1.4 mol/100 g and a weight-average molecular weight of 430, ex Shin-Etsu Chemical Co., Ltd.:

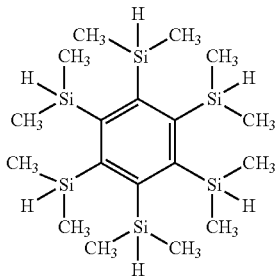 [SMILES: C[SiH](C)c1c([SiH](C)C)c([SiH](C)C)c([SiH](C)C)c([SiH](C)C)c1[SiH](C)C]

(B-6) Silphenylene skeleton-containing organic silicon compound which is represented by the following formula, and has a SiH group content of 1.3 mol/100 g and a weight-average molecular weight of 1,140, ex Shin-Etsu Chemical Co., Ltd.:

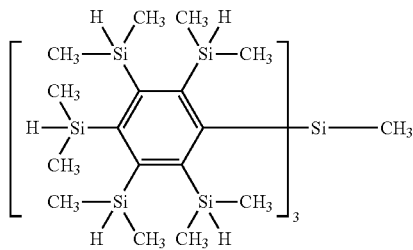

(B'-1) Organopolysiloxane which is represented by the following formula, and has a SiH group content of 0.90 mol/100 g and a weight-average molecular weight of 527, ex Shin-Etsu Chemical Co., Ltd.:

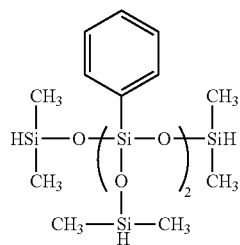

(D-1) Silphenylene monomer which is represented by the following formula, and has a SiH group content of 1.0 mol/100 g and a weight-average molecular weight of 198, ex Shin-Etsu Chemical Co., Ltd.:

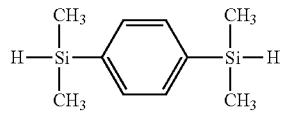

(D-2) Linear organopolysiloxane having hydrosilyl groups at both terminals, which is represented by the following formula, and has a SiH group content of 0.61 mol/100 g and a weight-average molecular weight of 341, ex Shin-Etsu Chemical Co., Ltd.:

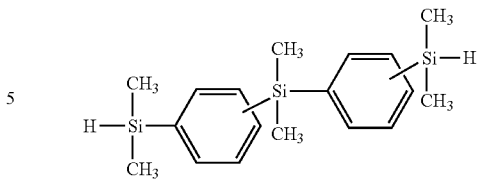

(D-3) Linear organopolysiloxane having hydrosilyl groups at both terminals, which is represented by the following formula, and has a SiH group content of 0.44 mol/100 g and a weight-average molecular weight of 536, ex Shin-Etsu Chemical Co., Ltd.:

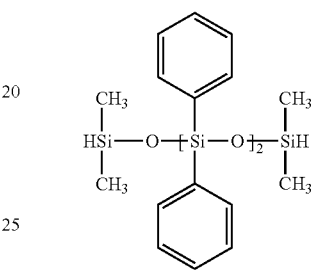

(C) Divinylsiloxane complex of chloroplatinic acid containing 2 mass % of platinum, ex Shin-Etsu Chemical Co., Ltd.

Examples 1 to 8 and Comparative Examples 1 to 4

The aforesaid components except the catalyst were mixed in the amounts as described in Tables 1 and, then, the catalyst (C) was added in an amount, as a platinum metal, of 2 ppm relative to the total mass of the composition, to obtain a curable resin composition. The curable resin compositions prepared in Examples 1 to 8 and Comparative Examples 1 to 4 were evaluated according to the following manners. The results are as shown in tables 2 and 3. In table 1, the H/Vi is a ratio of the total number of the hydrosilyl groups to the total number of the vinyl groups in the composition.

[1. Viscosity of the Curable Resin Compositions]

The viscosity of the curable resin composition was determined with a B-type viscometer at 23 degrees C. according to the Japanese Industrial Standards (JIS) Z 8803:2011. The results are as shown in Tables 2 and 3.

[2. Volatile and Nonvolatile Components in the Curable Resin Compositions]

Approximately 1.5 grams of the curable resin composition was poured into an aluminum petri dish having a diameter of 50 mm and a depth of 10 mm and, then, heated at 150 degrees C. for 1 hours to obtain a cured product. The masses before and after curing were precisely measured. The masses of the volatile components and the nonvolatile cured components were calculated from the masses before and after heating. The volatile content and the nonvolatile content shown in Tables 2 and 3 are percentages, relative to the amount of the curable resin composition before heating.

[3. Hardness of the Cured Products]

The curable resin composition was poured into an aluminum petri dish having a diameter of 50 mm and a depth of 10 mm and, then, heated at 60 degrees C. for one hour, 100 degrees C. for one hour and, subsequently 150 degrees C. for 4 hours to obtain a cured product. A hardness of the cured product was determined with a durometer type D according to the Japanese Industrial Standards (JIS) K 6253-3:2012. The results are as shown in Tables 2 and 3.

[4. Light Transmittance of the Cured Products]

A U-shape Teflon (Trademark) spacer having a space of 40 mm width, 15 mm height and 1 mm depth was sandwiched between two glass slides having dimensions of 50 mm×20 mm×1 mm at the both sides of the spacer and they were tightly held. The curable resin composition was poured into the space and heated at 60 degrees C. for one hour, subsequently at 100 degrees C. for one hour and, then, at 150 degrees C. for four hours, to obtain a cured sample having thickness of 1 mm. A transmittance at 450 nm of the sample was determined with a spectrophotometer, U-4100, ex Hitachi High-Technologies Corporation. The results are as shown in Tables 2 and 3.

[5. Tensile Strength and Elongation at Break of the Cured Products]

The curable resin composition was poured into a Teflon-coated mold having a cavity of 150 mm×200 mm×2 mm, and heated stepwise at 60 degrees C. for one hour, 100 degrees C. for one hour and, subsequently 150 degrees C. for 4 hours to obtain a sample. A tensile strength and an elongation at break of the cured product were determined according to JIS K 6251:2010 with a tensile tester EZ TEST, EZ-L, ex Shimadzu Corporation, in the following conditions: a head speed was 500 mm/min, a distance between clamps was 80 mm, and a distance of gauge points was 40 mm. The results are as shown in Tables 2 and 3.

[6. Curing Rate]

The change of the storage elastic modulus G' in Pa of the curable resin composition at 80 degrees C. with time was determined by a testing apparatus, ALPHA TECHNOLOGIES APA 2000, and the value of Tan δ derived from the obtained value of the storage elastic modulus was plotted with time. The peak top time was read from the graph and was taken as a gelation time. The measurement was carried out at a frequency of 100 cpm and an amplitude angle of 0.750. The results are as shown in Tables 2 and 3.

[7. Thermal Cycle Test]

The curable resin composition was dispensed on a Tiger3528 package, ex Shin-Etsu Chemical Co., Ltd., and heated at 60 degrees C. for one hour, 100 degrees C. for one hour and, subsequently 150 degrees C. for 4 hours to cure. In this way, 20 sample packages encapsulated with the cured product were obtained. The 20 encapsulated packages were subjected to a thermal cycle test (TCT) with 1000 thermal cycles of from −50 degrees C. to 140 degrees C. and then in a reversed way. The test samples which had cracks was counted. The results are as shown in Tables 2 and 3.

TABLE 1

| | | Ex. 1 | Ex. 2 | Ex. 3 | Ex. 4 | Ex. 5 | Ex. 6 | Ex. 7 | Ex. 8 | Com. Ex. 1 | Com. Ex. 2 | Com. Ex. 3 | Com. Ex. 4 |
|---|---|---|---|---|---|---|---|---|---|---|---|---|---|
| (A) | (A-1) | 80 | 80 | 80 | 50 | 50 | 50 | | | 80 | 80 | 80 | 80 |
| | (A-2) | | | | | | | 70 | 50 | | | | |
| | (A-3) | 20 | 20 | 20 | | | | 30 | 50 | 20 | 20 | 20 | 20 |
| | (A-4) | | | | 50 | | 50 | | | | | | |
| | (A-5) | | | | | 50 | | | | | | | |
| (B) | (B-1) | 12.7 | 9.3 | 19.8 | | | | | | | | | |
| | (B-2) | | | | 4.3 | | | | | | | | |
| | (B-3) | | | | | 15.6 | | | | | | | |
| | (B-4) | | | | | | 2.2 | | | | | | |
| | (B-5) | | | | | | | 2.5 | | | | | |
| | (B-6) | | | | | | | | 2.3 | | | | |
| | (B'-1) | | | | | | | | | 8.3 | 9.3 | 6.5 | |
| (D) | (D-1) | | | | | | | | | | | 6.5 | |
| | (D-2) | 12.7 | | | 4.3 | 15.6 | 8.8 | 22.1 | 9.4 | 8.3 | | | 20.5 |
| | (D-3) | | 9.3 | | | | | | | | 9.3 | | |
| (C) | | 2 ppm as platinum, relative to a total amount of the composition | | | | | | | | | | | |
| H/Vi | | 1 | 1 | 1.8 | 0.7 | 2.5 | 1.1 | 1.2 | 1.2 | 1 | 1 | 1 | 1 |

TABLE 2

| | | | | Ex. 1 | Ex. 2 | Ex. 3 | Ex. 4 | Ex. 5 | Ex. 6 | Ex. 7 | Ex. 8 |
|---|---|---|---|---|---|---|---|---|---|---|---|
| Evaluation | Viscosity | 23 degrees C. | Pa·s | 2.2 | 5.2 | 3.1 | 2.6 | 2 | 3.2 | 4 | 2.8 |
| | Nonvolatile content | 150 degrees C., 1 hr | % | 99.6 | 99.4 | 99.5 | 99.6 | 99.8 | 99.8 | 99.7 | 99.8 |
| | Volatile content | 150 degrees C., 1 hr | % | 0.4 | 0.6 | 0.5 | 0.4 | 0.2 | 0.2 | 0.3 | 0.2 |
| | Hardness | Shore D | — | 64 | 52 | 71 | 25 | 45 | 22 | 73 | 38 |
| | Transmittance | thickness of 1 mm, 450 nm | % T | 99.7 | 99.7 | 99.6 | 99.8 | 99.6 | 99.7 | 99.7 | 99.6 |
| | Tensile strength | 25 degrees C. | MPa | 12 | 6.7 | 22 | 3.3 | 5.4 | 3 | 26 | 4.4 |
| | Elongation at break | 25 degrees C. | % | 60 | 70 | 30 | 150 | 100 | 160 | 30 | 120 |
| | Gelation time | 80 degrees C. | min | 4 | 6 | 2 | 5 | 4 | 5 | 5 | 5 |
| | Thermal cycle test | 1000 thermal cycles of −50 to/from 140 degrees C. | Number of the cracked samples | 0/20 | 0/20 | 0/20 | 0/20 | 0/20 | 0/20 | 0/20 | 0/20 |

TABLE 3

| Evaluation | | | Com. Ex. 1 | Com. Ex. 2 | Com. Ex. 3 | Com. Ex. 4 |
|---|---|---|---|---|---|---|
| Viscosity | 23 degrees C. | Pa·s | 5.6 | 5.8 | 5.8 | 5.5 |
| Nonvolatile content | 150 degrees C., 1 hr | % | 99.7 | 99.3 | 97.2 | 99.7 |
| Volatile content | 150 degrees C., 1 hr | % | 0.3 | 0.7 | 2.8 | 0.3 |
| Hardness | Shore D | — | 50 | 42 | 35 | 55 |
| Transmittance | thickness of 1 mm, 450 nm | % T | 99.7 | 99.8 | 99.6 | 99.6 |
| Tensile strength | 25 degrees C. | MPa | 5.6 | 3.2 | 2.6 | 7.5 |
| Elongation at break | 25 degrees C. | % | 50 | 40 | 20 | 70 |
| Gelation time | 80 degrees C. | min | 5 | 6 | 6 | 14 |
| Thermal cycle test | 1000 thermal cycles of −50 to/from 140 degrees C. | Number of the cracked samples | 15/20 | 16/20 | 20/20 | 0/20 |

As shown in Table 3, the curable resin compositions of Comparative Examples 1, 2 and 3 comprising the polyfunctional SiH type organopolysiloxane having no silphenylene skeleton were excellent in a curing rate, but inferior in mechanical strengths and showed the poor crack resistance in the TCT test. In addition, the curable resin composition of Comparative Example 3 comprising the silphenylene monomer had the large volatile content derived from the silphenylene monomer, which was deviated from the initial composition, and the obtained cured product was brittle. In the curable resin composition of Comparative Example 4 comprising the silphenylene oligomer having only two SiH groups, the volatile content was small and the crack resistance was excellent, but the curability was inferior. On the other hand, the curable resin composition of the present invention has the excellent curing rate and quickly provides a cured product having excellent mechanical strengths as shown in Examples 1 to 8.

The present curable resin composition comprising the organic silicon compound which has the silphenylene skeleton and three or more SiH groups has the excellent curing rate and provides a cured product having the high toughness.

INDUSTRIAL APPLICABILITY

The curable resin composition of the present invention has the excellent curability and the obtained cured product has the good mechanical properties. Therefore, the curable resin composition of the present invention is used, for example, for encapsulating a semiconductor element to thereby improve its productivity. Further, the curable resin composition gives a cured product having a high optical transparency and an excellent mechanical strengths and, therefore, is usable as a material for encapsulating an LED element, in particular, a blue LED or an ultraviolet LED.

The invention claimed is:

1. A curable resin composition comprising the following components (A) to (C):
   (A) an organic silicon compound having at least two alkenyl groups in a molecule,
   (B) an organic silicon compound represented by the following formula (1) in an amount such that a ratio of the number of the hydrosilyl groups in component (B) to the number of the alkenyl groups in component (A) is 0.4 to 4,

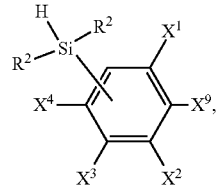

(1)

wherein $R^2$ is, independently of each other, a hydrogen atom or a monovalent hydrocarbon group having 1 to 12 carbon atoms and all of the $X^1$ to $X^4$ and $X^9$ are a group represented by the following formula (1'),

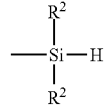

(1')

wherein $R^2$ is as defined above, and
   (C) a hydrosilylation catalyst in a catalytic amount.

2. The curable resin composition according to claim 1, wherein component (A) is an organic silicon compound represented by the following formula (4):

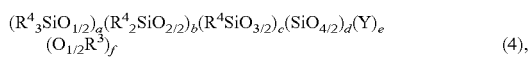

$$(R^4{}_3SiO_{1/2})_a(R^4{}_2SiO_{2/2})_b(R^4SiO_{3/2})_c(SiO_{4/2})_d(Y)_e(O_{1/2}R^3)_f \quad (4),$$

wherein $R^4$ is, independently of each other, a monovalent hydrocarbon group having 1 to 12 carbon atoms and optionally having an unsaturated bond, provided that at least two of $R^4$ are an alkenyl group, $R^3$ is a hydrogen atom or a monovalent hydrocarbon group having 1 to 6 carbon atoms, a is an integer of from 0 to 100, b is an integer of from 0 to 1,000, c is an integer of from 0 to 500, d is an integer of from 0 to 500, e is an integer of from 0 to 500, f is an integer of from 0 to 50, a total of a, b, c, d and e is 2 to 1,000, and Y is a silphenylene unit which has a valance of 1 to 26 and is represented by the following formula (II),

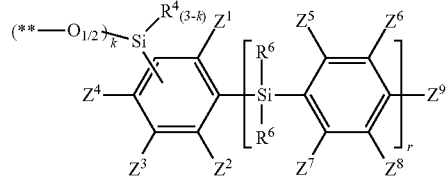

(II)

wherein r is 0 or 1, k is an integer of from 1 to 3, a bonding marked with ** in the formula (II) bonds to a silicon atom of another siloxane in the formula (4), $R^4$ is as defined above, $Z^1$ to $Z^9$ are, independently of each other, a hydrogen atom, a monovalent hydrocarbon group having 1 to 6 carbon atoms, a divalent, trivalent or tetravalent group represented by the following formula (5'), a monovalent group represented by the following formula (5"), or a group having a valance of 1 to 16 and represented by the following formula (7'), $R^6$ is, independently of each other, selected from the groups defined for $R^4$ or a group which has a valance of 1 to 16 and is represented by the following formula (6'),

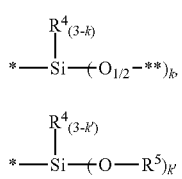
(5')

(5")

wherein a bonding marked with * in the formulas (5') and (5") bonds to a carbon atom of the benzene ring, a bonding marked with ** in the formula (5') bonds to a silicon atom of another siloxane in the formula (4), k is an integer of from 1 to 3, k' is an integer of from 1 to 3, $R^4$ is as defined above, and $R^5$ is a monovalent hydrocarbon group having 1 to 6 carbon atoms,

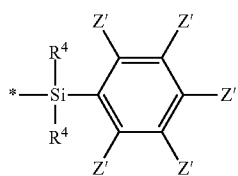
(7')

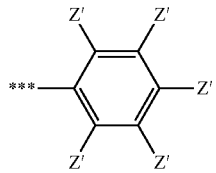
(6')

wherein Z' is, independently of each other, a hydrogen atom, a monovalent hydrocarbon group having 1 to 6 carbon atoms or the group represented by the formula (5') or (5"), $R^4$ is as defined above, a bonding marked with * in the formula (7') bonds to a carbon atom of the benzene ring and a bonding marked with *** in the formula (6') bonds to a silicon atom of another siloxane in the formula (4).

3. A curable resin composition comprising the following components (A) to (C):

(A) an organic silicon compound having at least two alkenyl groups in a molecule, (B) an organic silicon compound represented by the following formula (2) in an amount such that a ratio of the number of the hydrosilyl groups in component (B) to the number of the alkenyl groups in component (A) is 0.4 to 4;

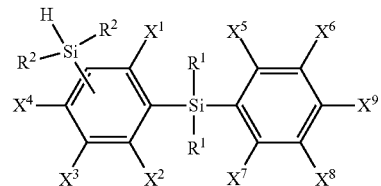
(2)

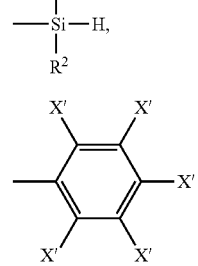
(1')

(4')

wherein $R^1$ is, independently of each other, a hydrogen atom, a monovalent hydrocarbon group having 1 to 12 carbon atoms or the group represented by the formula (4'), $R^2$ is independently of each other, a hydrogen atom or a monovalent hydrocarbon group having 1 to 12 carbon atoms, $X^1$ to $X^9$ and X' are, independently of each other, a hydrogen atom, a monovalent hydrocarbon group having 1 to 6 carbon atoms or the group represented by the formula (1'), and at least two of $X^1$ to $X^9$ and X' are the group represented by the formula (1'), and (C) a hydrosilylation catalyst in a catalytic amount.

4. A curable resin composition comprising the following components (A) to (C):

(A) an organic silicon compound having at least two alkenyl groups in a molecule, (B) an organic silicon compound represented by the following formula (3) in an amount such that a ratio of the number of the hydrosilyl groups in component (B) to the number of the alkenyl groups in component (A) is 0.4 to 4;

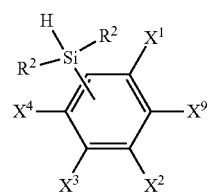
(3)

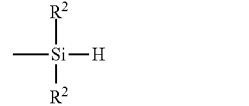
(1')

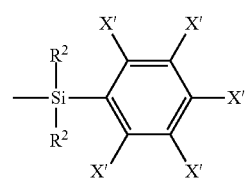
(3')

wherein $R^2$ is, independently of each other, a hydrogen atom or a monovalent hydrocarbon group having 1 to 12 carbon atoms, $X^1$ to $X^4$ and $X^9$ are, independently of each other, a hydrogen atom, a monovalent hydrocarbon group having 1 to 6 carbon atoms or the group represented by the formula (1') or (3'), X' is, independently of each other, a hydrogen atom, a monovalent hydrocarbon group having 1 to 6 carbon atoms or the group represented by the formula (1'), at least two of $X^1$ to $X^4$ and $X^9$ are the group represented by the formula (3') and at least two of $X^1$ to $X^4$, $X^9$ and X' are the group represented by the formula (1'), and (C) a hydrosilylation catalyst in a catalytic amount.

5. A semiconductor device provided with a cured product obtained by curing the curable resin composition according to claim 1 or 2.

6. The curable resin composition according to claim 3, wherein component (A) is an organic silicon compound represented by the following formula (4):

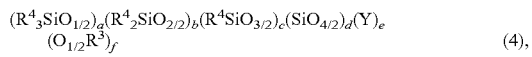

wherein $R^4$ is, independently of each other, a monovalent hydrocarbon group having 1 to 12 carbon atoms and optionally having an unsaturated bond, provided that at least two of $R^4$ are an alkenyl group, $R^3$ is a hydrogen atom or a monovalent hydrocarbon group having 1 to 6 carbon atoms, a is an integer of from 0 to 100, b is an integer of from 0 to 1,000, c is an integer of from 0 to 500, d is an integer of from 0 to 500, e is an integer of from 0 to 500, f is an integer of from 0 to 50, a total of a, b, c, d and e is 2 to 1,000, and Y is a silphenylene unit which has a valance of 1 to 26 and is represented by the following formula (II),

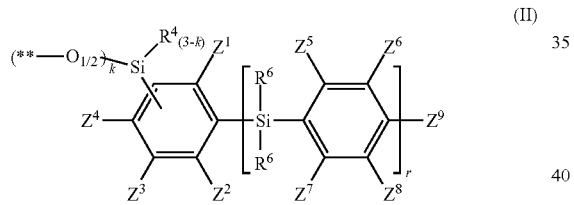

wherein r is 0 or 1, k is an integer of from 1 to 3, a bonding marked with ** in the formula (II) bonds to a silicon atom of another siloxane in the formula (4), $R^4$ is as defined above, $Z^1$ to $Z^9$ are, independently of each other, a hydrogen atom, a monovalent hydrocarbon group having 1 to 6 carbon atoms, a divalent, trivalent or tetravalent group represented by the following formula (5'), a monovalent group represented by the following formula (5"), or a group having a valance of 1 to 16 and represented by the following formula (7'), $R^6$ is, independently of each other, selected from the groups defined for $R^4$ or a group which has a valance of 1 to 16 and is represented by the following formula (6'),

wherein a bonding marked with * in the formulas (5') and (5") bonds to a carbon atom of the benzene ring, a bonding marked with ** in the formula (5') bonds to a silicon atom of another siloxane in the formula (4), k is an integer of from 1 to 3, k' is an integer of from 1 to 3, $R^4$ is as defined above, and $R^5$ is a monovalent hydrocarbon group having 1 to 6 carbon atoms,

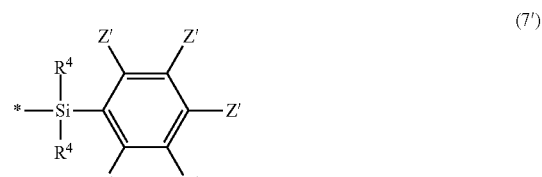

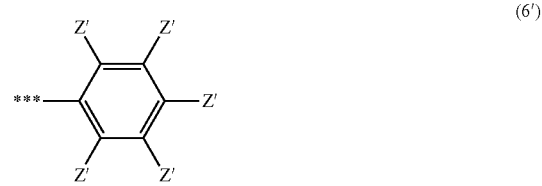

wherein Z' is, independently of each other, a hydrogen atom, a monovalent hydrocarbon group having 1 to 6 carbon atoms or the group represented by the formula (5') or (5"), $R^4$ is as defined above, a bonding marked with * in the formula (7') bonds to a carbon atom of the benzene ring and a bonding marked with *** in the formula (6') bonds to a silicon atom of another siloxane in the formula (4).

7. The curable resin composition according to claim 4, wherein component (A) is an organic silicon compound represented by the following formula (4):

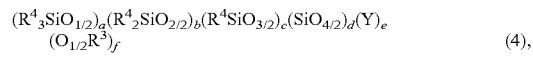

wherein $R^4$ is, independently of each other, a monovalent hydrocarbon group having 1 to 12 carbon atoms and optionally having an unsaturated bond, provided that at least two of $R^4$ are an alkenyl group, $R^3$ is a hydrogen atom or a monovalent hydrocarbon group having 1 to 6 carbon atoms, a is an integer of from 0 to 100, b is an integer of from 0 to 1,000, c is an integer of from 0 to 500, d is an integer of from 0 to 500, e is an integer of from 0 to 500, f is an integer of from 0 to 50, a total of a, b, c, d and e is 2 to 1,000, and Y is a silphenylene unit which has a valance of 1 to 26 and is represented by the following formula (II),

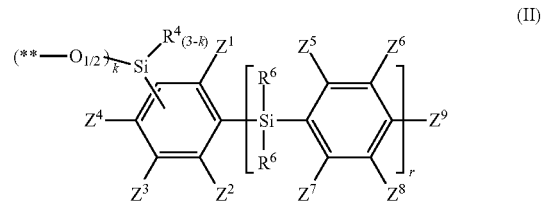

wherein r is 0 or 1, k is an integer of from 1 to 3, a bonding marked with ** in the formula (II) bonds to a silicon atom of another siloxane in the formula (4), $R^4$ is as defined above, $Z^1$ to $Z^9$ are, independently of each other, a hydrogen atom, a monovalent hydrocarbon group having 1 to 6 carbon atoms, a divalent, trivalent or tetravalent group represented by the following formula (5'), a monovalent group represented by the following formula (5"), or a group having a valance of 1 to 16 and represented by the following formula (7'), $R^6$ is, independently of each other, selected from the groups defined for $R^4$ or a group which has a valance of 1 to 16 and is represented by the following formula (6'),

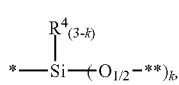
(5')

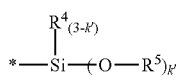
(5")

wherein a bonding marked with * in the formulas (5') and (5") bonds to a carbon atom of the benzene ring, a bonding marked with ** in the formula (5') bonds to a silicon atom of another siloxane in the formula (4), k is an integer of from 1 to 3, k' is an integer of from 1 to 3, $R^4$ is as defined above, and $R^5$ is a monovalent hydrocarbon group having 1 to 6 carbon atoms,

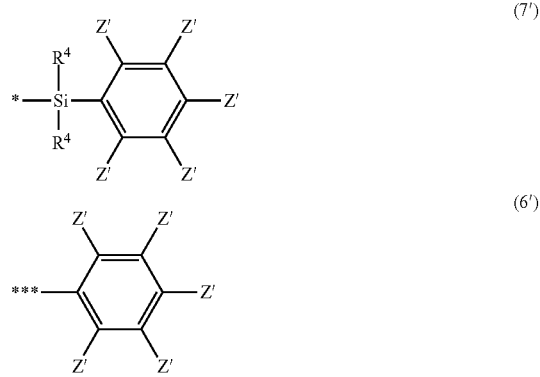

wherein Z' is, independently of each other, a hydrogen atom, a monovalent hydrocarbon group having 1 to 6 carbon atoms or the group represented by the formula (5') or (5"), $R^4$ is as defined above, a bonding marked with * in the formula (7') bonds to a carbon atom of the benzene ring and a bonding marked with *** in the formula (6') bonds to a silicon atom of another siloxane in the formula (4).

8. A semiconductor device provided with a cured product obtained by curing the curable resin composition according to claim 3 or 6.

9. A semiconductor device provided with a cured product obtained by curing the curable resin composition according to claim 4 or 7.

* * * * *